United States Patent [19]
Pacey

[11] Patent Number: 6,142,144
[45] Date of Patent: Nov. 7, 2000

[54] INTUBATION INSTRUMENT

[76] Inventor: John A. Pacey, 6290 Collingwood Street, Vancouver B.C., Canada, V6N 1T6

[21] Appl. No.: 09/060,891

[22] Filed: Apr. 15, 1998

Related U.S. Application Data

[60] Provisional application No. 60/067,205, Dec. 1, 1997, and provisional application No. 60/074,355, Feb. 10, 1998.

[51] Int. Cl.⁷ .................................................. A61M 16/00
[52] U.S. Cl. ................................ 128/200.26; 128/207.14
[58] Field of Search ........................ 128/200.26, 207.14, 128/207.15, 206.29, 911, 912, DIG. 26; 600/187, 188, 190, 194, 199

[56] References Cited

U.S. PATENT DOCUMENTS

| | | |
|---|---|---|
| 3,771,514 | 11/1973 | Huffman . |
| 4,126,127 | 11/1978 | May . |
| 4,592,343 | 6/1986 | Upsher . |
| 4,832,004 | 5/1989 | Heckele . |
| 4,846,153 | 7/1989 | Berci . |
| 4,947,896 | 8/1990 | Bertlett . |
| 4,982,729 | 1/1991 | Wu . |
| 5,016,614 | 5/1991 | MacAllister ...................... 128/200.26 |
| 5,038,766 | 8/1991 | Parker . |
| 5,095,888 | 3/1992 | Hawley . |
| 5,174,283 | 12/1992 | Parker . |
| 5,183,031 | 2/1993 | Rossoff . |
| 5,203,320 | 4/1993 | Augustine . |
| 5,261,392 | 11/1993 | Wu . |
| 5,329,940 | 7/1994 | Adair . |
| 5,339,805 | 8/1994 | Parker . |
| 5,381,787 | 1/1995 | Bullard . |
| 5,431,152 | 7/1995 | Flam et al. . |
| 5,443,058 | 8/1995 | Ough . |
| 5,498,231 | 3/1996 | Franicevic . |
| 5,513,627 | 5/1996 | Flam . |
| 5,551,946 | 9/1996 | Bullard . |
| 5,603,688 | 2/1997 | Upsher . |
| 5,607,386 | 3/1997 | Flam ................................. 128/200.26 |
| 5,636,625 | 6/1997 | Miyagi et al. ..................... 128/200.26 |
| 5,645,519 | 7/1997 | Lee et al. . |
| 5,665,052 | 9/1997 | Bullard . |
| 5,676,635 | 10/1997 | Levin . |

FOREIGN PATENT DOCUMENTS

WO 98/41137  9/1998  WIPO .

OTHER PUBLICATIONS

Flexible Laryngoscopes, 1 page specification sheet, Richard Wolf Gmbh, Circa, Mar. 1997.

Adjustable Laryngo–pharyngoscope, 1 page specification sheet, Richard Wolf GmbH, Circa Apr. 1997.

Primary Examiner—Aaron J. Lewis
Assistant Examiner—Teena Mitchell
Attorney, Agent, or Firm—ipsolon, LLP

[57] ABSTRACT

The configuration and arrangement of the instrument greatly facilitate safe placement of the instrument and an associated endotracheal tube. The instrument provides a path for guiding movement of the endotracheal tube in a manner that permits the distal end of the tube to move along the instrument directly toward the glottis. The instrument includes a passage into which a telescope is mounted. The arrangement of the guide path and passageway ensure that the advancing end of the tube remains observable as it is advanced to the glottis. Suction is provided to remove fluid etc that would otherwise obscure the view of the tube.

15 Claims, 3 Drawing Sheets

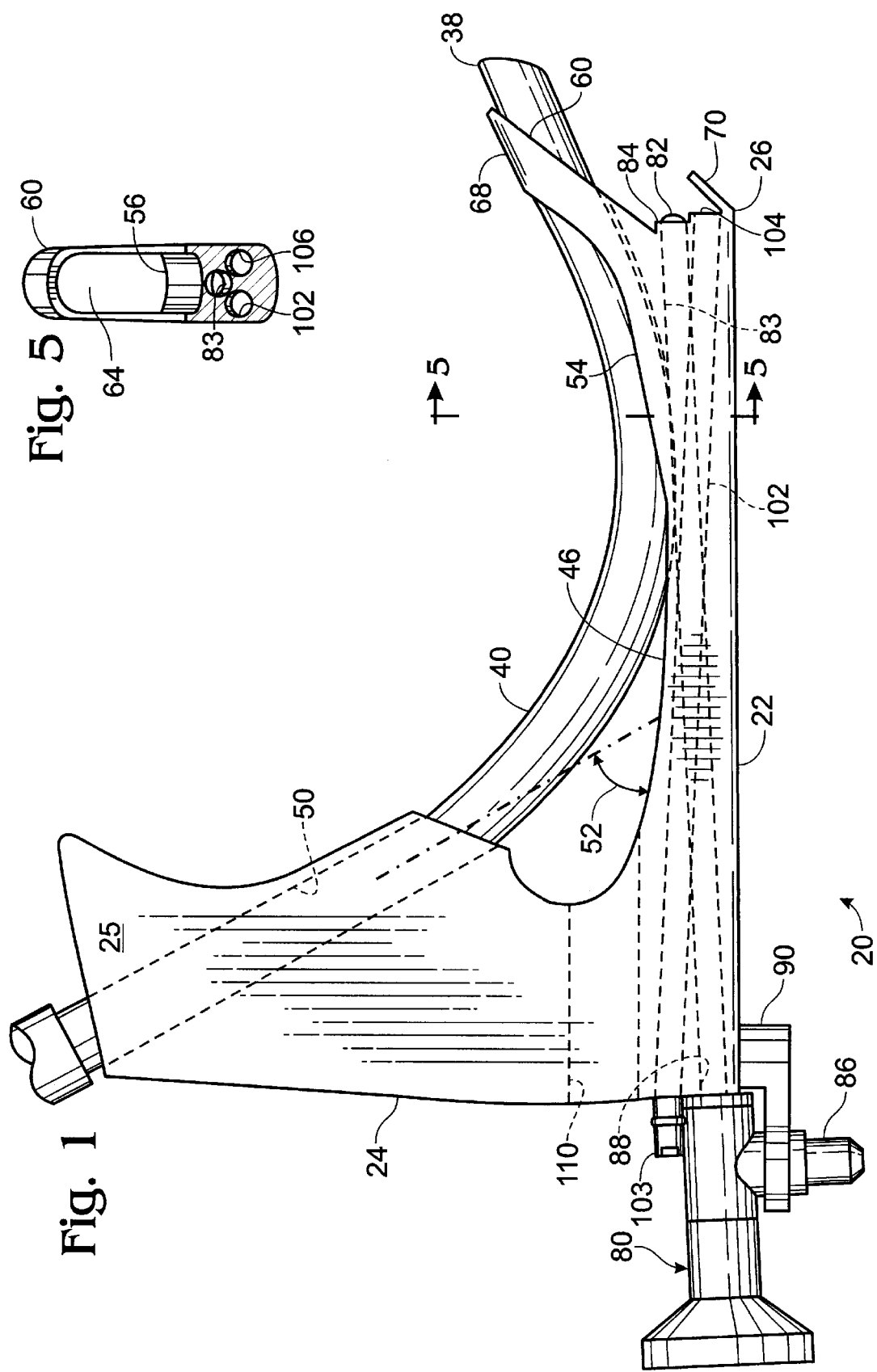

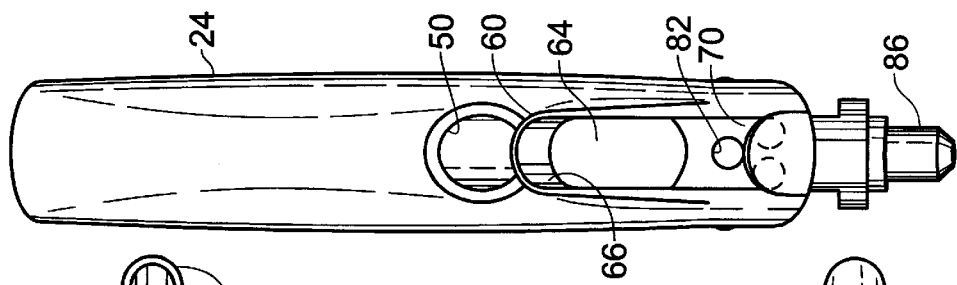
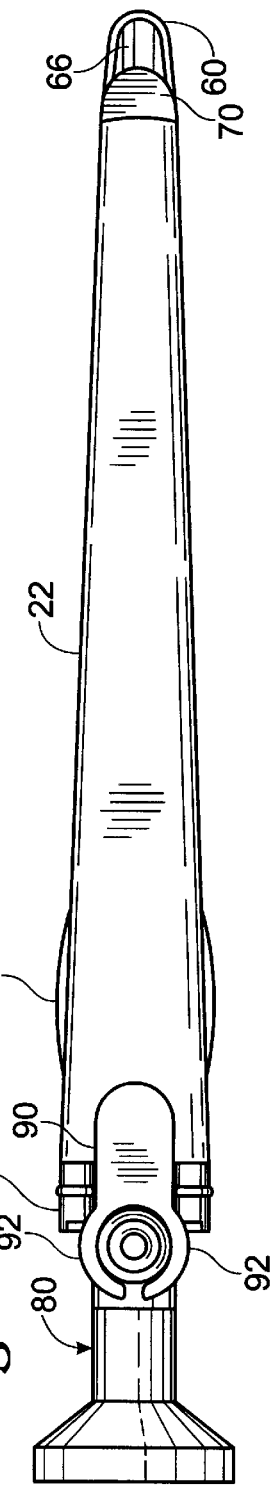
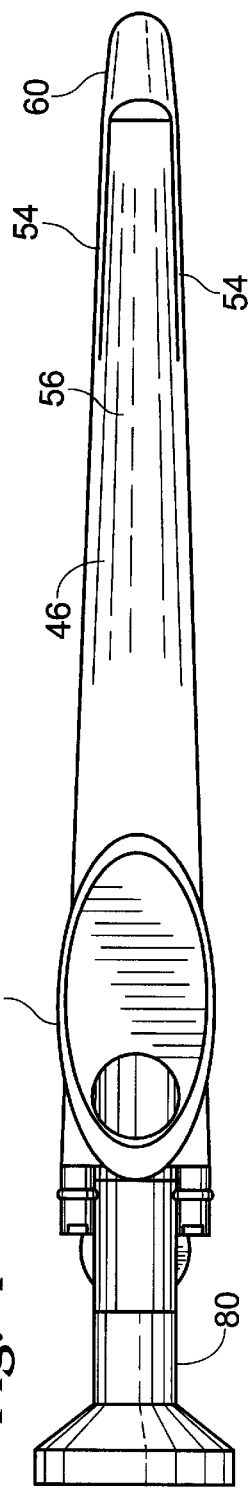

INTUBATION INSTRUMENT

REFERENCE TO RELATED APPLICATIONS

This application claims the benefit of U.S. Provisional Application Nos. 60/067,205, filed Dec. 1, 1997 and 60/074,355, filed Feb. 10, 1998.

FIELD OF THE INVENTION

This invention relates to endoscopic instruments, particularly to an intubation instrument, such as a laryngoscope.

BACKGROUND AND SUMMARY OF THE INVENTION

Intubation of the human trachea is carried out daily in operating rooms and emergency facilities in order to facilitate respiration of a patient. The goal of the intubation process is to locate the distal end of an endotracheal tube in the larynx with the proximal end outside the patient's mouth.

Safe and effective intubation requires controlled insertion of the endotracheal tube so that the tube is directed to the upper part of the larynx, the glottis, without damaging or being blocked by the patient's tissue. To this end, intubation instruments have been developed. Such instruments generally provide a somewhat rigid structure that is inserted into the mouth of the patient so that the distal end of the instrument is located in the glottis, adjacent to the vocal cords. An endotracheal tube is slid through the instrument during or after insertion of the instrument.

Advanced intubation instruments provide a lighted telescope or fiber optic viewing device. The telescope is carried by the instrument with the objective lens located at the distal end of the instrument and arranged so that the user may, via the proximal, viewing end of the telescope, observe the advancement of the instrument and the endotracheal tube. Such instruments are normally referred to as laryngoscopes.

In designing such intubation instruments it is important to provide a configuration that permits quick location of the instrument and tube without injurious or fatal delay that may occur with repeated attempts.

Precisely locating an endotracheal tube is certainly critical. Facial and neck trauma or the presence of blood, excoriation, mucus etc. may cause misdirection of the tube into the patient's esophagus.

The present invention provides an intubation device that includes a configuration and arrangement of components that greatly facilitate rapid, safe placement of the instrument and associated endotracheal tube.

In accordance with one aspect of this invention, the instrument provides a path for guiding movement of the endotracheal tube in a manner that permits the distal end of the tube to move along the instrument directly toward the glottis. The instrument includes a passage into which a telescope is mounted. The arrangement of the guide path and passage ensures that the distal end of the tube remains observable as it is advanced to the glottis.

The observation of the movement of the instrument and tube is enhanced by the creation of a clearing at the distal end of the instrument. In this regard, the instrument includes structure for establishing a clearing at the distal end of the instrument, into which clearing the patient's tissue is prevented from entering. The inner end of the telescope is located at this clearing, as well as advantageously placed suction tube(s) for ensuring that the clearing remains free of fluid and vapor that would otherwise obstruct the operator's view.

The structure used for establishing the clearing includes a protrusion that is configured to engage or lift the patient's epiglottis, thereby to expose the glottis. Moreover, a projecting guard is included for establishing the clearing. The guard is angled in a manner that permits smooth, sliding movement of the instrument across tissue to the desired, inserted position of the instrument.

In preferred embodiments of the invention, the instrument may include a second fluid passageway for delivering fluid to or from the distal end of the instrument. Moreover, the instrument can be configured to provide a channel for guiding secondary instruments, such as forceps, for clearly observed removal of foreign material in the larynx.

Other advantages and features of the present invention will become clear upon study of the following portion of this specification and drawings.

BRIEF DESCRIPTION OF THE DRAWINGS

FIG. 1 is a side, elevation view of a preferred embodiment of an instrument made in accordance with the invention shown carrying an endotracheal tube.

FIG. 2 is a front elevation view of the instrument shown with the endotracheal tube removed for clarity.

FIG. 3 is a bottom plan view of the instrument.

FIG. 4 is a top plan view of the instrument.

FIG. 5 is a cross section taken about line 5—5 of FIG. 1.

DETAILED DESCRIPTION OF PREFERRED EMBODIMENTS

Figure 6:
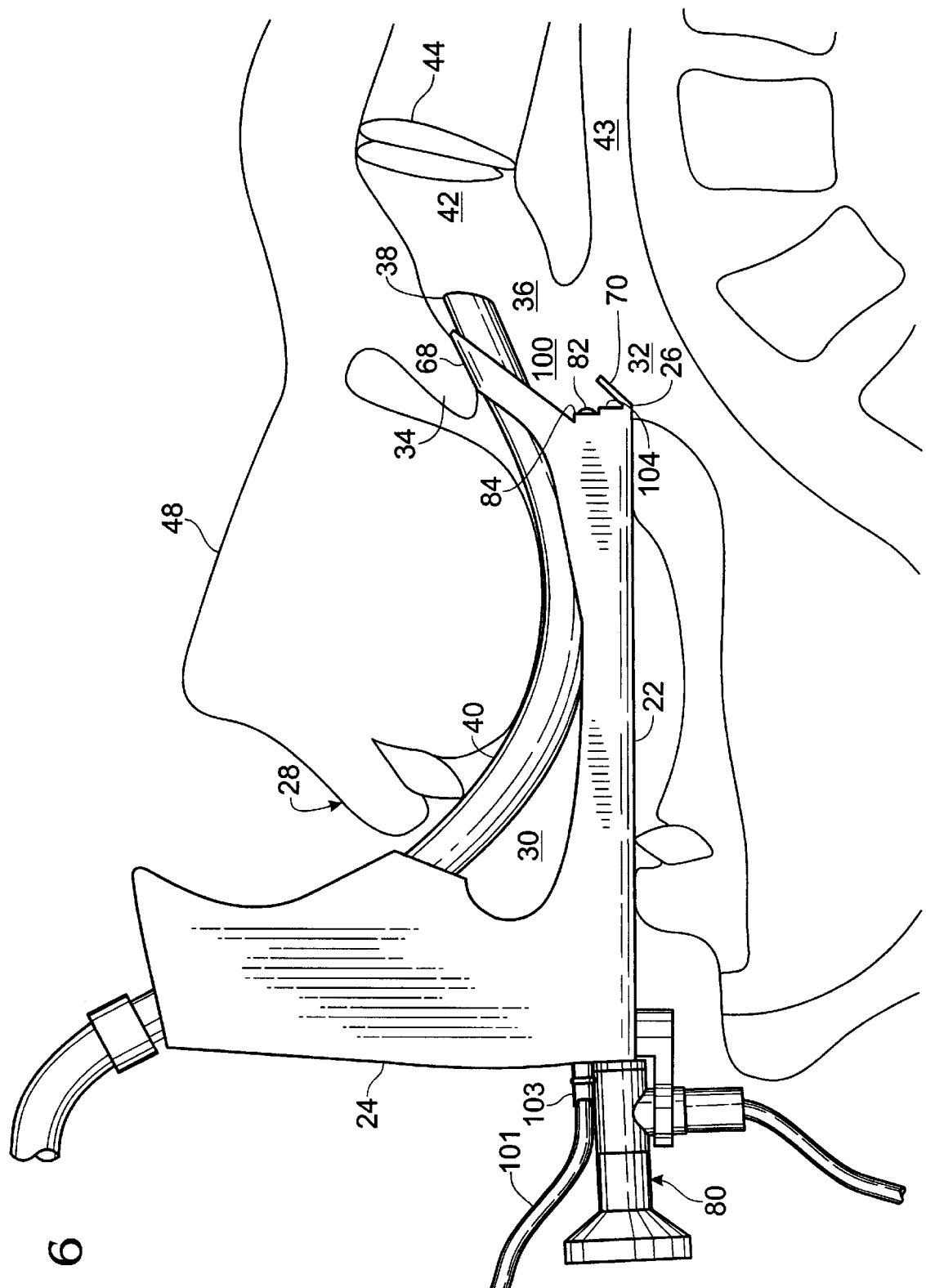
FIG. 6 is a side view of the instrument shown inserted into the mouth of a patient.

With particular reference to FIGS. 1 and 6, a preferred embodiment of an intubation instrument made and used in accord with the present invention includes a body 20 that generally comprises an elongated arm 22 with integrally attached handle 24. The instrument is preferably formed from metal or rigid plastic that can withstand sterilization.

The instrument arm has a distal end 26 that is inserted into the mouth 30 of a patient 28. Preferably, the instrument is inserted while the patient is recumbent, face-up, with the head tipped slightly backwardly, supported in what is known as the sniffing position. Before proceeding with the description of the instrument, it will be useful here to identify the relevant components of the human patient (FIG. 6).

As noted, the instrument is inserted, distal end 26 first, through the patient's mouth 30. As explained below, when properly inserted, the distal end of the endotracheal tube 40 resides in the hypopharynx 32. The patient's epiglottis 34 is supported by the instrument in a manner to expose the glottis 36. In the present invention, the instrument provides for the telescopically observed advance of the leading end 38 of an endotracheal tube 40 through the glottis 36, into the larynx 42 adjacent to the vocal cords 44. As is known in the art, an endotracheal tube 40 permits air to be conducted to and from an incapacitated patient. The present instrument includes a number of features that greatly increase the ease with which the instrument 20 and tube 40 can be properly located and continuously observed via a telescope or other optic device.

More particularly, the arm 22 of the instrument 20 is configured to define in the handle 24 and on its anterior surface 46 a guide path for the smooth advance of the tube 40 relative to the inserted instrument 20. For the purpose of this description, the anterior surface 46 of the instrument is, as shown if FIG. 6, that facing the lower jaw 48 of the intubated patient.

The guide path includes a portion consisting of a channel 50 (FIG. 1) that is formed through the handle 24. It is noteworthy that the handle 24 extends in a generally perpendicular orientation relative to the elongated arm 22. The channel 50, however, extends through the handle 24 at a direction that is generally oblique to the length of the handle 24 and to the arm 22. Put another way, the channel orientation 50 is such that after the leading end of the tube 40 is advanced through the channel 50, it emerges to contact the anterior surface 46 of the instrument at an acute angle 52 to slide along that surface toward the distal end 26 of the instrument.

Approaching the distal end of the instrument, the opposing anterior side edges 54 are gradually built up to define, in combination with the anterior surface part between the edges 54 a groove 56 that is generally curved in cross section, as best shown in FIG. 5. Preferably, the radius of curvature of the groove 56 generally conforms to the outside diameter of the tube 40. As such, the leading end of the tube 40 is precisely and smoothly guided through this groove 56, which makes up another part of the above mentioned guide path.

The side edges 54 terminate in a loop 60 that is part of the instrument and protrudes from the distal end 26 of the instrument at an angle of about 45 degrees relative to the length of the arm 22. As viewed from the end (FIGS. 2 and 5), the loop defines an elongated opening 64 through which extends the leading end 38 of the tube 40.

Here it is useful to note that an endotracheal tube 40 used with the preferred embodiment of the instrument is formed of flexible plastic tubing. One such tube is that manufactured by Mallinckrodt, Inc. of St. Louis Mo., under the trademark Mallinckroft. The tube is constructed to assume a curved configuration when relaxed, although it is readily deformed as needed. In the present invention, the loop 60 is configured to permit the leading end 38 of the tube 40 to approach its curved, relaxed configuration as it passes through and out of the loop 60.

More particularly, the elongated opening 64 (elongated, that is, in the direction away from the anterior surface of the arm 22, as shown in FIGS. 2 and 5) permits the flexible tube 40 to resile away from the distal end 26 of the arm 22 to seat against the underside 66 of the loop 60, as shown in FIG. 1. This underside 66 is curved to conform to the outside diameter of the tube, thereby providing, in a manner similar to the above-mentioned groove 56, precise and smooth guidance of the tube through the loop 60. Thus, the loop makes up another part of the above mentioned guide path. The advantages of the just described tube movement are discussed more fully below.

The loop 60 includes a surface 68 that bears against the patient's epiglottis 34 when the instrument is fully inserted. As a result, the epiglottis 34 and surrounding tissue are held by the instrument in a position where they do not occlude the glottis 36.

A guard 70 extends from the bottom of the instrument arm 22 at the distal end thereof. The guard is an extension of the arm 22 and is angled upwardly (as viewed in FIGS. 1 and 6) to present an underlying surface that acts like a skid upon insertion of the instrument to permit the distal end of the instrument to be advanced against the patient's tissue without damage to the tissue. Thus, the guard 70 reduces the effort needed to insert the device, while protecting the patient's tissue.

Once the arm 22 is in place, the guard 70 serves to prevent the tissue in the hypopharynx 32 from contacting the distal end 26 of the arm 22 and obstructing the view available to a telescope 80 that is carried by the instrument. In this regard, the telescope 80 is one that terminates in a long tubular member having an objective lens at its end 82. The terminus of the telescope fits into a telescope passage 83 that is formed through the arm 22. The telescope also includes a light post 86 that is mounted to the telescope 80 near the outer end 88 of the passage 83 and that provides illumination to the telescope 80. In a preferred embodiment of the instrument, a suitable telescope is one having approximately a 25-degree viewing angle; such as manufactured by Henke-Sass, Wolf of America Inc., Southbridge, Mass., as model number 8853.42.

In a preferred embodiment of the invention the instrument is provided with a clip 90 that is mounted to the arm 22 near the outer end of the passageway 83. The clip 90 includes two spaced-apart, arched arms 92 that spread apart slightly to releasably receive between them the generally cylindrical shaped light post 86 as the telescope is slid into position relative to the instrument 22. The clip 90, therefore, serves to retain the telescope in the correct location and within the telescope passage 83 during use. Moreover, since the arms 92 of the clip engage a radial projection of the telescope (namely, the light post 86), the telescope is held against inadvertent rotation out of the desired orientation relative to the arm 22. The arms 92 of the clip 90 are resilient and readily move apart to release the light post 86 when the telescope is pulled from the instrument for replacement and cleaning.

Returning to consider the distal end 26 of the arm 22, the end 82 of the telescope 80 is located at the inner end 84 of the passage 83 when the telescope is installed. As noted, the guard 70 prevents tissue from contacting the end of the telescope. More particularly, the telescope-guarding or tissue-retracting effect of both the loop 60 and the guard 70 has the effect of establishing a clearing 100 (FIG. 6), which is a space between the guard and loop, adjacent to the distal end of the instrument and free of view-obstructing tissue. The inner end 84 of the telescope passage (hence, the end 82 of an installed telescope) is in this clearing 100. Thus, the telescope is unaffected by tissue that would otherwise obstruct, at least in part, the telescopic view of the advancing, leading end 38 of the endotracheal tube 40.

As noted earlier, the loop 60 configuration is such that the tube that extends from the loop tends to assume its relaxed, curved shape. The leading end 38, therefore, tends to veer upwardly (considering FIG. 6) toward the glottis 36 and away from what would be a dangerous entry into the patient's esophagus 43.

The tube 40 is carried on the anterior surface 46 of the arm 22, between the patient's lower jaw and the telescope passage 83. This orientation, in combination with the curved guide path of the tube 40 ensure that the advancing, leading end 38 of the tube remains in the field of view of the telescope (as does the glottis) without crossing near the end 82 of the telescope, which crossing would obscure the view of the tube vis-a-vis the glottis 36.

For example, if the lens carried in the end 82 of the telescope is angled upwardly to provide a view in a direction toward the glottis 36, the movement of the tube end 38 out from beneath the underside of the loop 60 will be nearly parallel to a line defining the center of the field of view of the telescope. It has been found that this relative positioning of the telescope end 82 and tube end 38 greatly enhances viewing of the advancing tube as compared to instruments that went before.

The preciseness with which the present instrument may be inserted enables one to supply, during insertion, intermittent pulses of air (positive pressure) through the tube 40 to provide immediate respiration to the patient during the insertion process. Thus, the conventional air or oxygen supply to the tube may be so connected and controlled during insertion of the instrument.

The clearing 100 would be susceptible to entry of fluids such as blood, exudate, mucus etc, which might be present in instances of neck trauma. In accord with another aspect of this invention, there is provided efficient suction removal of such matter. To this end, the arm 22 is provided with a passageway 102 having an interior end 104 that opens at the distal end 26 of the instrument, below the inner end 84 of the telescope passage 83. A suction tube 101 (FIG. 6) may be attached to a connector 103 that is mounted to the instrument at the outer end of the passageway 102. Suction is applied for removing any fluid that may begin to accumulate in the clearing 100. It is noteworthy that the instrument is arranged so that the inner end of the telescope passage is above (FIG. 1) the interior end 104 of the suction passageway 102. Thus, the end 104 of the suction passageway resides in what may be called a sump portion of the clearing 100. Unwanted fluids are removed before reaching a level that would obscure the end 82 of an installed telescope 80.

It is contemplated that suction would be applied to the clearing 100 even in the absence of view-obstructing fluids because the application of suction would tend to cool the telescope (which is heated by the light source) or remove vapor that might otherwise tend to condense on the lens of the telescope.

In a preferred embodiment, another passageway 106 (FIG. 5) is provided in the arm in a manner that substantially matches the suction passageway 102. This other passageway is available to hold another suction tube (thus enhancing overall suction of the clearing 100) or, alternatively, gas such as oxygen could be directed through this passageway 106 to increase the oxygen content of the glottis area.

The suction applied by one or both passages 102, 106 provides a vortex of fluid flow in the vicinity of the inner end 84 of the telescope passage, thereby providing a particularly effective way to remove from the telescope end (lens) 82 any fluid contamination, such as blood, that would otherwise obscure the view through the telescope. Thus, the telescope need not be removed for clearing the lens.

It will be appreciated that the arrangement of the various components of the instrument presents an instrument that is substantially symmetrical about the long axis of the arm and handle. Thus the instrument is readily useable by a right- or left-handed operator.

It is also contemplated that the channel 50 in the handle 24 may be configured to open on one side of the handle, such as surface 25 (FIG. 1) thereby forming the channel 50 as a groove in the handle. As a result, the tube 40 could be inserted laterally into the channel/groove. At the junction of the channel 50 and surface 25, the groove width could be narrowed somewhat, relative to the remainder of the groove, to a width just slightly narrower than the diameter of the flexible tube 40. Such a configuration permits the tube to be secured by a snap-fit into this configuration of the channel.

While the present invention has been described in terms of a preferred embodiment, it will be appreciated by one of ordinary skill that the spirit and scope of the invention is not limited to those embodiments, but extend to the various modifications and equivalents as defined in the appended claims. For example, the above-described telescope could be replaced with a fiber optic device or a video camera. Moreover, additional channels could be provided for delivering other devices to the distal end of the instrument. FIG. 1 shows in dashed lines 110 such an alternative channel that would permit the advance of elongated forceps to the distal end of the instrument to be used, for example, in removing foreign objects from the larynx.

What is claimed is:

1. An intubation instrument, a portion of which is for insertion into a patient through the patient's mouth, comprising:

a body having a handle attached thereto;

an arm attached to the body, the arm having a distal end and being arranged for insertion distal-end first through a patient's mouth and having an anterior surface that faces a patient's lower jaw when the arm is inserted;

a telescope passage carried by the arm and having an inner end located at the distal end of the arm; and a guide path formed on the anterior surface of the instrument body and configured for guiding the sliding movement of an endotracheal tube along the anterior surface between the telescope passage and a patient's lower jaw, wherein the guide path includes a loop protruding from the distal end of the arm, through which loop an endotracheal tube is extendable.

2. The instrument of claim 1 wherein the loop defines an elongated opening through which the endotracheal tube is extendable, the protruding loop being arranged so a leading end of the endotracheal tube is free to move away from the distal end of the arm while remaining in the opening.

3. The instrument of claim 2 wherein the portion of the loop opening away from the arm is shaped to conform to the outside diameter of the endotracheal tube and wherein that portion of the opening combines with the remainder of the guide path away from the loop to permit the endotracheal tube to assume a curved orientation at the distal end of the arm.

4. The instrument of claim 1 wherein the arm is of a length such that the distal end of the arm is adjacent to a patient's glottis when the arm is inserted and wherein the loop protrudes from the distal end of the arm by an amount sufficient to bear against a patient's epiglottis.

5. The instrument of claim 1 further comprising a suction passageway formed in the arm and having an interior end located at the distal end of the arm such that the inner end of the telescope passage is substantially between the interior end of the suction passageway and the anterior surface of the arm.

6. The instrument of claim 5 further comprising a guard connected to the distal end of the arm and projecting distally therefrom with respect to the interior end of the suction passageway thereby to prevent contact between the interior end of the suction passageway and a patient's tissue.

7. The instrument of claim 5 further comprising another passageway formed in the arm for conducting fluid to or from the distal end of the arm.

8. An intubation instrument, a portion of which is for insertion into a patient through the patient's mouth, comprising:

a body having a handle attached thereto;

an arm attached to the body, the arm having a distal end and being arranged for insertion distal-end first through a patient's mouth and having an anterior surface that faces a patient's lower jaw when the arm is inserted;

a telescope passage carried by the arm and having an inner end located at the distal end of the arm;

a guide path formed on the anterior surface of the instrument body and configured for guiding the sliding movement of an endotracheal tube along the anterior surface between the telescope passage and a patient's lower jaw; and a guard connected to the distal end of the arm and extending distally therefrom with respect to the inner end of the telescope passage thereby to prevent contact between the inner end of the telescope passage and tissue of a patient into whom the arm is inserted.

9. The instrument of claim 8 wherein the guide path includes a loop protruding from the distal end of the arm, through which loop a leading end of an endotracheal tube is extendable, the loop extending distally from the arm with respect to the inner end of the telescope passage so that adjacent to the inner end of the telescope passage there is established between the guard and the loop a clearing into which a patient's tissue is prevented from entry when the arm is inserted.

10. The instrument of claim 8 wherein the guard is angled relative to the arm in a direction toward the anterior surface of the arm thereby to facilitate insertion of the arm into the mouth of a patient.

11. An intubation instrument, a portion of which is for insertion into a patient through the patient's mouth, comprising:

a body having a handle attached thereto;

an arm attached to the body, the arm having a distal end and being arranged for insertion distal-end first through a patient's mouth and having an anterior surface that faces a patient's lower maw when the arm is inserted;

a telescope passage carried by the arm and having an inner end located at the distal end of the arm; and a guide path formed on the anterior surface of the instrument body and configured for guiding the sliding movement of an endotracheal tube along the anterior surface between the telescope passage and a patient's lower jaw; wherein the guide path includes a loop protruding from the distal end of the arm, through which loop an endotracheal tube is extendable; and wherein the handle is an elongated member that is substantially perpendicular to the arm and wherein the guide path includes a channel formed in the handle and through which channel an endotracheal tube may fit, wherein the length of the channel extends in a direction oblique to the arm and the handle thereby to permit the tube to assume a curved orientation away from the handle and along the anterior surface of the arm.

12. The instrument of claim 11 further comprising another channel formed in the handle, thereby to facilitate passage of a secondary instrument toward the distal end of the arm.

13. The instrument of claim 11 wherein the channel comprises a groove that opens to one side of the handle.

14. An intubation instrument, a portion of which is for insertion into a patient through the patient's mouth, comprising:

a body having a handle attached thereto;

an arm attached to the body, the arm having a distal end and being arranged for insertion distal-end first through a patient's mouth and having an anterior surface that faces a patient's lower jaw when the arm is inserted;

a telescope passage carried by the arm and having an inner end located at the distal end of the arm; and a guide path formed on the anterior surface of the instrument body and configured for guiding the sliding movement of an endotracheal tube along the anterior surface between the telescope passage and a patient's lower jaw; and wherein the telescope passage includes an outer end through which a telescope may be passed into the telescope passage, the instrument including a clip mounted near the outer end for releasably retaining a telescope in the telescope passage.

15. The instrument of claim 14 wherein the clip includes arms that are arranged to engage a radially projecting part of the telescope, thereby to restrict rotation of the telescope relative to the telescope passage.

* * * * *